(12) United States Patent
Griessbach et al.

(10) Patent No.: US 8,371,183 B2
(45) Date of Patent: Feb. 12, 2013

(54) METHOD FOR DETERMINING PROPERTIES OF THREE-DIMENSIONAL OBJECTS

(76) Inventors: Volker Griessbach, Chemnitz (DE); Soeren Griessbach, Chemnitz (DE)

(*) Notice: Subject to any disclaimer, the term of this patent is extended or adjusted under 35 U.S.C. 154(b) by 176 days.

(21) Appl. No.: 12/452,552

(22) PCT Filed: Jul. 8, 2008

(86) PCT No.: PCT/DE2008/001126
§ 371 (c)(1),
(2), (4) Date: Jun. 4, 2010

(87) PCT Pub. No.: WO2009/006884
PCT Pub. Date: Jan. 15, 2009

(65) Prior Publication Data
US 2010/0249977 A1    Sep. 30, 2010

(30) Foreign Application Priority Data

Jul. 10, 2007   (DE) .......................... 10 2007 032 439

(51) Int. Cl.
*G01N 19/00* (2006.01)
(52) U.S. Cl. ...................................... 73/865.9
(58) Field of Classification Search .................. None
See application file for complete search history.

(56) References Cited

U.S. PATENT DOCUMENTS

| | | | |
|---|---|---|---|
| 5,397,538 A | 3/1995 | Stark et al. | |
| 7,059,665 B2 * | 6/2006 | Murai et al. | 296/181.2 |
| 2007/0097360 A1 | 5/2007 | Beaume | |
| 2007/0183918 A1 | 8/2007 | Monsheimer et al. | |

FOREIGN PATENT DOCUMENTS

| | | |
|---|---|---|
| DE | 43 03 858 | 8/1994 |
| DE | 44 14 775 | 10/1995 |
| DE | 195 27 446 | 10/1996 |
| DE | 196 45 377 | 5/1998 |
| DE | 198 46 325 | 4/2000 |
| DE | 100 57 686 | 6/2002 |
| DE | 10 2004 012 682 | 10/2005 |
| WO | WO 92/11577 | 7/1992 |

* cited by examiner

Primary Examiner — Robert R Raevis
(74) Attorney, Agent, or Firm — Collard & Roe, P.C.

(57) ABSTRACT

The invention relates to a method for determining properties of three-dimensional objects that have been produced by a generative method, in particular by a thermal generative method. The problem solved is that of providing a nondestructive test method by which the density of such objects can be determined and possible component defects can be identified. This is achieved by firstly completely immersing the three-dimensional object in a dyeing liquor, removing it from the dyeing liquor after a defined residence time, then washing it off, drying it and exposing it to a vacuum and subsequently subjecting it to an image-analytical evaluation by determining the intensity of the coloration by apparatus technology, wherein an assessment with regard to density and component defects of the three-dimensional object is effected by a comparison of the image-analytical characteristic values of coloration and reference data stored beforehand by computer technology.

6 Claims, 1 Drawing Sheet

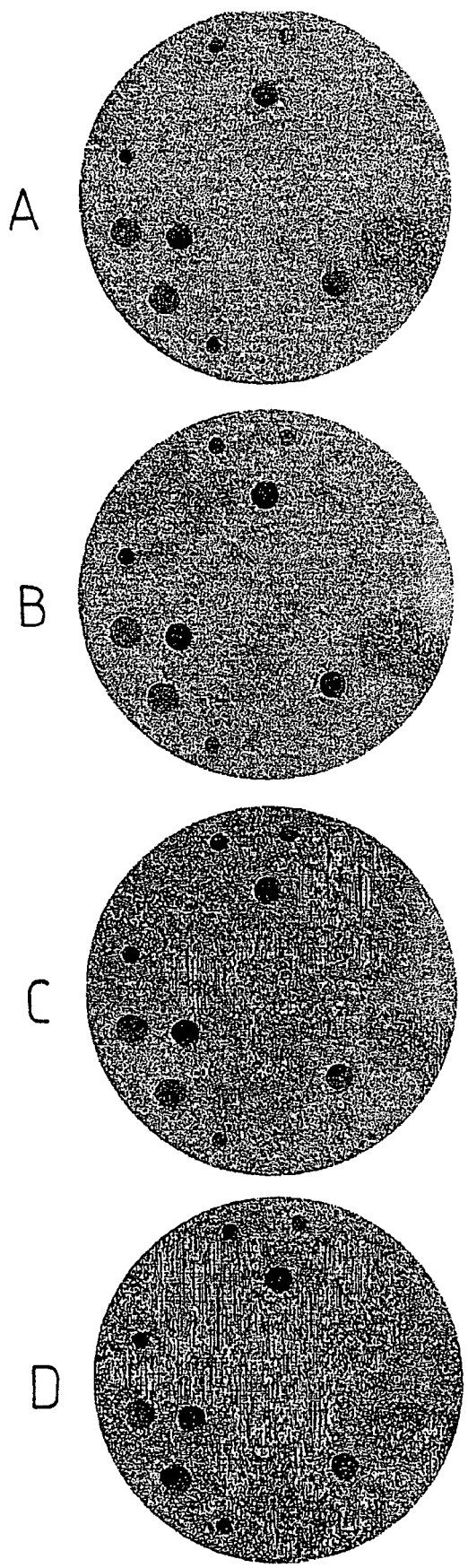

METHOD FOR DETERMINING PROPERTIES OF THREE-DIMENSIONAL OBJECTS

CROSS REFERENCE TO RELATED APPLICATIONS

This application is the National Stage of PCT/DE2008/001126 filed on Jul. 8, 2008, which claims priority under 35 U.S.C. §119 of German Application No. 10 2007 032 439.3 filed on Jul. 10, 2007. The international application under PCT article 21(2) was not published in English.

BACKGROUND OF THE INVENTION

1. Field of the Invention

The invention relates to a method for determining properties of three-dimensional objects that were produced using a thermal generative method, particularly using a thermal generative method, for example by means of laser sintering, FDM (Fused Deposition Modeling), or SMS (Selective Mask Sintering).

2. The Prior Art

"Rapid technologies" are used for numerous technical fields. Technologies in this regard, using stereolithography on the basis of photopolymerization, are known from WO 92/11 577 A 1 and DE 44 14 775 A 1. In this connection, three-dimensional objects are produced by means of locally limited chemical reactions, in that liquid monomers or oligomers are crosslinked to produce a solid polymer, by means of applying UV radiation. Buildup of these three-dimensional objects takes place in layers. As soon as a layer has been produced photochemically and polymerized, new liquid material is applied to this layer, and also polymerized afterwards, so that another layer is formed.

In laser sintering, a 3D CAD file is transformed into a 2D file, by means of cutting it into thin layers having a thickness of typically 0.10 mm to 0.15 mm, and afterwards transmitted to the process computer. This computer controls the IR radiation that scans the surface of the powder layer, depending on the contour of the 2D data, by means of a system of optical lenses and mirrors. In this connection, the powder is sintered in a layer, with point precision. After a layer has been processed, the construction platform is lowered in accordance with the selected layer thickness, and a new layer of powder is applied. Thus, a three-dimensional object is generated layer by layer. A system in this regard is known, for example, from DE 10 2004 012 682 A 1.

Aside from laser sintering, the technical solutions called FDM (Fused Deposition Modeling) and SMS (Selective Mask Sintering) are also increasingly being used as thermal generative methods.

Independent of the concrete embodiment of method sequence and device technology, such thermal generative methods have fundamentally proven themselves. After the use of these methods was extensively restricted to the production of prototypes during the development process, at first, this technique is also increasingly being used for mass production of products in small and medium piece numbers. Thus, shorter development times, faster production introduction times ("time to market") and often better quality of the products in question can be achieved, in comparison with conventional methods.

Despite these undisputed advantages, the use of thermal generative methods is problematic, at least for mass production of safety-relevant components. Components for machines, systems, land vehicles, or aircraft must withstand greatly varying stresses. The usability and useful lifetime of these components is often limited by process-related variation in density or by the occurrence of cracks at critical locations of the construction, which depend on numerous influence factors, such as, for example

- unforeseeable or uncontrollable process variations,
- geometric peculiarities of the components,
- material variations when changing lots or due to changes in climatic conditions,
- overload due to mechanical, thermal and/or chemical stresses, especially of the surfaces.

This mutual dependence and the influences that cannot be precisely foreseen lead to greatly different prognoses concerning the ability to withstand stress and the useful lifetime of the components that can actually be achieved. It is true that such components can be tested with regard to density and strength by means of measurements regarding the geometrical parameters and by means of weight determination. However, smaller defects within a layer or within a small component area are not detected with such tests.

In this connection, studies by the applicant have shown that in the case of thermal generative methods (e.g. laser sintering system with a temperature of 175° C. in the work area), even slight temperature differences of 1° K to 3° K bring about differences in density on the order of 5% to 10%. With reference to the aforementioned working temperature, deviations in the process parameters of only 1% to 2% will therefore result in density differences of up to 10%. If it is furthermore taken into consideration that a density that differs by about 10% can cause a strength loss of up to 50%, it becomes obvious that there is a significant demand for the development of a method for destruction-free determination of typical material parameters of three-dimensional objects, with which method even small structural defects can be determined. However, such a method has not become available up to the present. Even a transfer of test methods in other technical fields to the thermal generative methods that might be considered by a person skilled in the art does not yield any suitable solution approach.

For example, DE 198 46 325 A 1 describes a technical solution for determining the effectiveness of sterilization of medical technology equipment using a chemo-indicator. This chemical substance brings about a change in color after a minimum action time of the necessary process parameters, whereby the end point of the color change is defined and described by the manufacturer. Accordingly, a statement concerning the effectiveness of the sterilization process is possible by means of a visual assessment of the indicator.

A device for optical evaluation of colorimetric discoloration zones on a carrier, for detection of components of a gas mixture in gas or vapor form, is known from DE 43 03 858 A 1. In this in-process inspection, light is transmitted through discoloration zones, which light either does or does not trigger a signal, by way of photocells. As a result, a statement concerning the progress of the discoloration zones when an established limit value is reached is achieved on the basis of the time sequence of these individual signals.

Although the aforementioned DE 198 46 325 A 1 and DE 43 03 858 A 1 have an interesting departure point, in that destruction-free component testing is implemented by means of evaluating color changes, these technical solutions are not suitable for thermal generative methods, in which significantly different material, temperature, and pressure conditions prevail. Furthermore, these methods only allow a general statement about whether or not a previously defined method point has been reached, in any case, but they do not allow the determination of specific material parameters.

SUMMARY OF THE INVENTION

It is the task of the invention to create a destruction-free testing method with which the density of three-dimensional objects produced by means of thermal generative methods can be determined, and possible component defects can be recognized.

This task is accomplished in that the three-dimensional object is first completely immersed into a dye bath, removed from the dye bath after a defined dwell time, and afterwards subjected to image-analysis evaluation, in that the intensity of the dyeing is determined by means of device technology, and whereby an evaluation of the density of the three-dimensional object takes place by means of a comparison of the image analysis characteristic values of the dyeing and of reference data previously stored by means of computer technology. Advantageous embodiments are the object of the dependent claims, whose technical characteristics will be described in greater detail in the exemplary embodiment.

By means of the technical solution according to the invention, a method is created with which the density and possible component defects of three-dimensional objects produced by means of thermal generative methods can be determined. In this connection, changes that can be measured in terms of color are evaluated by means of photo analysis.

When using this method, dyes diffuse into the three-dimensional object, in each instance, without the dimensions of the object changing. Dyeing of the three-dimensional object is achieved by means of the diffusion. Because of the properties of the proposed dyes, binding of these dyes to the structure of the three-dimensional object takes place by means of physical effects, without any change in the material properties. After the dwell time has been reached, the three-dimensional object is removed from the dye bath. Afterwards, excess dye is washed off, if necessary. An advantageous embodiment provides that the three-dimensional object is additionally dried. In this connection, application of a vacuum can take place, if necessary, as a result of which the water is evaporated and possible defects become particularly well visible. If drying in a vacuum takes place at a pressure of 1 to 5 mbar, deep cracks and density structures that lie deeper in the component become better visible. Afterwards, the actual evaluation of the three-dimensional object takes place, by means of evaluation of the color intensity. Thus, a testing technology for generatively produced components on the basis of diffusion dyeing becomes available, whereby the intensity of the penetration of the dye is an indication of the thickness and/or structure of the generatively produced layer, in each instance.

The method can be implemented, in cost-advantageous and reliable manner, by way of a personal computer in combination with a scanner or similar evaluation devices and suitable evaluation software. Immediate objective evaluation does not require any specially trained technical personnel, and the measurement result can be documented in fast and reliable manner. Depending on the concrete density, in each instance, and the defects of each generatively produced layer that might be present, differently intensive dyeing takes place. In the case of deviations that cannot be tolerated, which are an indication of component problems, error reports are produced by means of computer technology.

The diffusion dyeing of high-polymer components as described is a practical method for representing relevant changes in the surface resulting from variations in density and the formation of cracks, and is therefore particularly suited as a "prediction method" for components that are able to withstand long-term stress. The method can be used for different types of applications in which testing of three-dimensional objects produced in thermal generative manner with regard to density and component defects is required. Such visualization of different density structures is possible both immediately after the production process and during later studies concerning damage of high-polymer components subject to fatigue stress, whereby safety-relevant components are of particular interest.

DETAILED DESCRIPTION OF THE PREFERRED EMBODIMENTS

An exemplary embodiment of the invention will be described in the following:

When using the proposed method for determining parameters of three-dimensional objects that have been produced using a thermal generative method, for example by means of laser sintering, FDM (Fused Deposition Modeling), or SMS (Selective Mask Sintering), the three-dimensional object to be tested is first completely immersed in a dye bath. In a preferred embodiment, an aqueous dye solution is used as the dye bath; this is particularly advantageous in the case of polyamides. Also, the dye bath can have predominantly acid dyes (cationic dyes). The dye bath has temperatures between 50° Celsius and 95° Celsius.

After a defined dwell time, which preferably lies between 1.0 and 15.0 minutes, as a function of the concrete generative method, the concrete materials, and the dye bath used, in each instance, the three-dimensional object is removed from the dye bath, washed, dried, has vacuum (preferably at 1 to 5 mbar) applied to it, and finally is subjected to image analysis evaluation.

BRIEF DESCRIPTION OF THE DRAWINGS

In the drawing, four three-dimensional objects A, B, C, and D are shown, which have been treated and evaluated using the method according to the invention. These cylindrical objects have functionally required bores that can be seen in the drawing as small and dark dot surfaces, in each instance. The other darker surface sections, as compared with the color of the basic body, are the process-related dyed areas. Here, dyeing is present by about 1% in Object A, about 10% in Object B, about 50% in Object C, and about 80% of the component structure in Object D. Such dyeing is fundamentally an indication of possible density differences in the three-dimensional object, or of a completely defective density as compared with the density actually being aimed at, or of cracks in the component structure. The special dye solution diffuses more rapidly into the surface that has lower density and cracks, and dyes the componenet more intensively at the location of the problem than at the other component surfaces. Consequently, the intensively dyed component structures can be used to evaluate weak points and problems. In this connection, the intensity of the dyeing is determined by means of device technology, and afterwards an evaluation of the three-dimensional object takes place by means of a comparison of the image analysis characteristic values of the dyeing and of reference data previously stored by means of computer technology.

The invention claimed is:

1. Method for determining properties of three-dimensional objects that were produced using a thermal generative method, wherein the three-dimensional object is first completely immersed into a dye bath, removed from the dye bath after a defined dwell time, then washed, dried, and has vacuum applied to it, and afterwards subjected to image-analysis evaluation, in that the intensity of the dyeing is determined by means of device technology, whereby an evaluation with regard to density and component defects of the three-dimensional object takes place by means of a comparison of the image analysis characteristic values of the dyeing and of reference data previously stored by means of computer technology.

2. Method according to claim 1, wherein the dwell time of the three-dimensional object in the dye bath amounts to 1.0 to 15.0 minutes.

3. Method according to claim 1, wherein dye bath has temperatures between 50° Celsius and 95° Celsius.

4. Method according to claim 1, wherein the dye bath is an aqueous dye solution.

5. Method according to claim 1, wherein the dye bath predominantly has acid dyes (cationic dyes).

6. Method according to claim 1, wherein drying takes place under vacuum, at a pressure of 1 to 5 mbar.

* * * * *

UNITED STATES PATENT AND TRADEMARK OFFICE
CERTIFICATE OF CORRECTION

PATENT NO. : 8,371,183 B2
APPLICATION NO. : 12/452552
DATED : February 12, 2013
INVENTOR(S) : Griessbach et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 322 days.

Signed and Sealed this
First Day of September, 2015

Michelle K. Lee
*Director of the United States Patent and Trademark Office*